United States Patent [19]
Nobles et al.

[11] Patent Number: 5,385,572
[45] Date of Patent: Jan. 31, 1995

[54] TROCAR FOR ENDOSCOPIC SURGERY

[75] Inventors: Anthony A. Nobles, Fountain Valley; Arthur Lancaster, Costa Mesa; Robert J. Flower, Huntington Beach; Ben G. Brosch, Jr., Mission Viejo, all of Calif.

[73] Assignee: Beowulf Holdings, Los Angeles, Calif.

[21] Appl. No.: 974,956

[22] Filed: Nov. 12, 1992

[51] Int. Cl.⁶ .................. A61B 1/04; A61B 17/34
[52] U.S. Cl. .................. 606/185; 606/167; 128/4; 604/264
[58] Field of Search ................. 128/4, 6–8, 128/749, 395, 398; 607/90–93; 606/1, 167, 170, 184–186, 2, 10–16, 182, 183; 604/264, 164

[56] References Cited

U.S. PATENT DOCUMENTS

| | | | |
|---|---|---|---|
| 4,254,762 | 3/1981 | Yoon . | |
| 4,269,192 | 5/1981 | Matsuo | 128/6 |
| 4,273,127 | 6/1981 | Auth et al. | 606/16 |
| 4,535,773 | 8/1985 | Yoon | 604/51 |
| 4,566,438 | 1/1986 | Liese et al. | 128/6 |
| 4,740,047 | 4/1988 | Abe et al. | 606/2 |
| 4,832,979 | 5/1989 | Hoshino | 606/16 |
| 5,151,096 | 9/1992 | Khoury | 606/15 |
| 5,196,005 | 3/1993 | Doiron et al. | 606/15 |
| 5,215,526 | 6/1993 | Deniega et al. | 604/264 |
| 5,234,450 | 8/1993 | Segalowitz | 606/170 |
| 5,246,436 | 9/1993 | Rowe | 606/13 |
| 5,250,068 | 10/1993 | Ideguchi et al. | 606/185 |
| 5,271,380 | 12/1993 | Riek et al. | 128/4 |

FOREIGN PATENT DOCUMENTS 2102678  2/1983  United Kingdom ............. 606/167

*Primary Examiner*—Ralph A. Lewis
*Assistant Examiner*—Glenn K. Dawson
*Attorney, Agent, or Firm*—Gilliam, Duncan, Harms

[57] ABSTRACT

A trocar has an elongated shaft, and a cutting element is attached to a distal end of the shaft. The cutting element can be a transparent puncturing head formed integrally with the shaft, and a distal portion of the puncturing head is configured as a regular triangular pyramid having three sharpened cutting edges. Alternatively, the cutting element can be three or four metal cutting blades which are attached to the distal end of the shaft. In either case, a pathway for light communication is established from the cutting element through the shaft, a portion of which is transparent. The shaft has a cavity, and a rigid endoscope is positioned in the cavity to collect light from the distal end of the shaft. A video monitor is connected to the endoscope for displaying an image of the path of advancement of the trocar.

7 Claims, 5 Drawing Sheets

FIG. 10
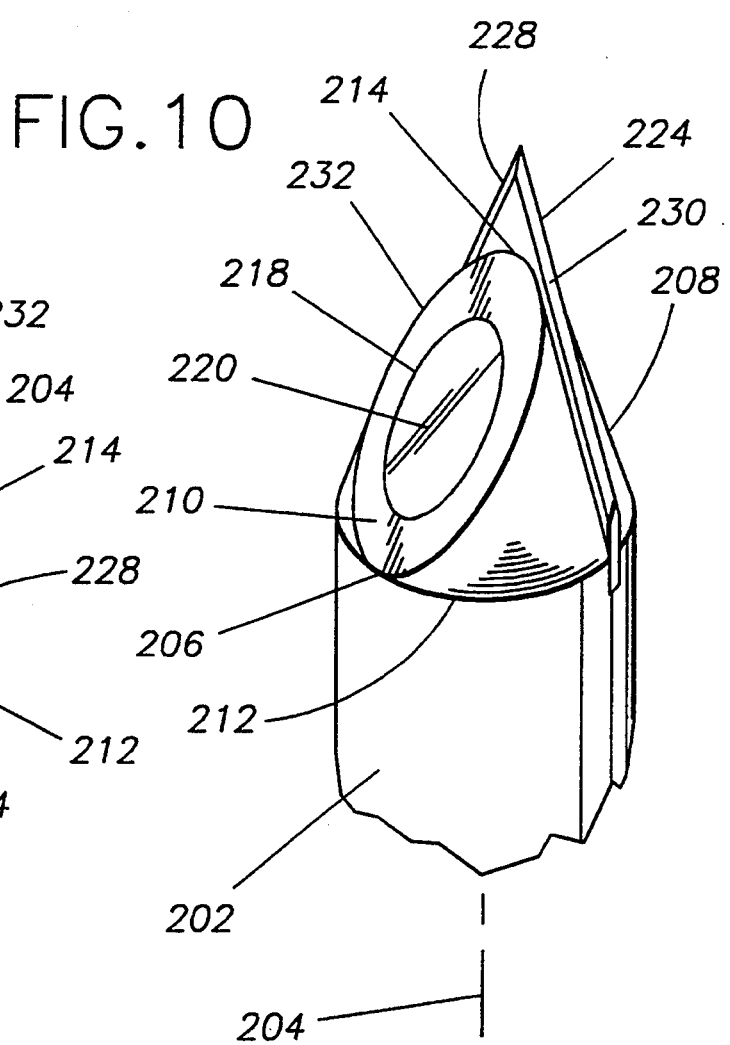
FIG. 12
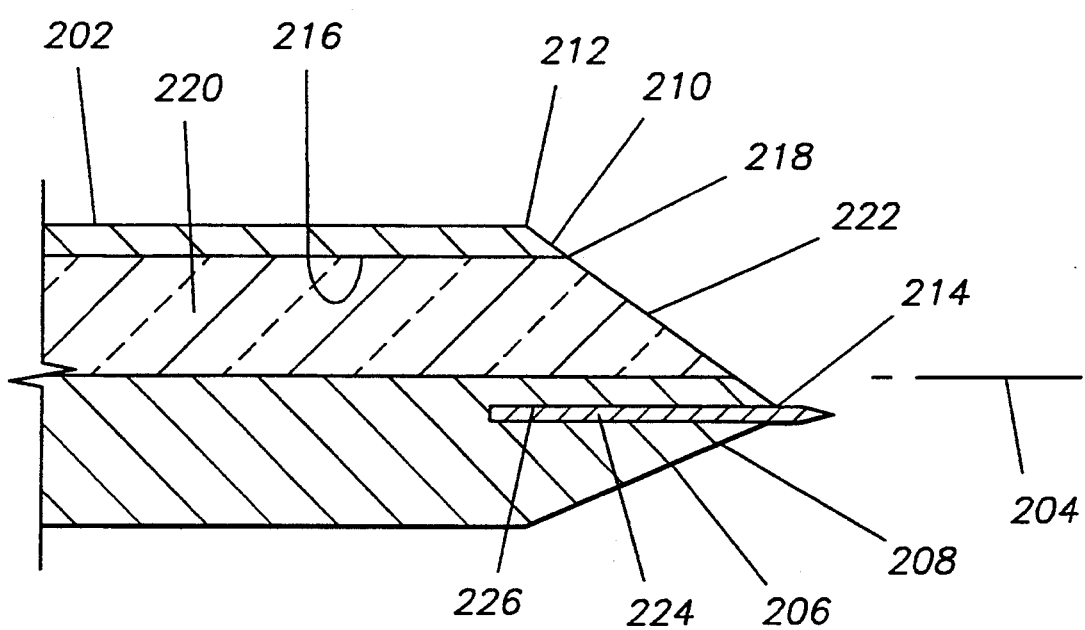
FIG. 11

TROCAR FOR ENDOSCOPIC SURGERY

FIELD OF THE INVENTION

The present invention relates generally to instruments for endoscopic surgery and more particularly to trocars for laparascopic surgery.

BACKGROUND

Laparascopic surgery is a genre of endoscopic surgery which is used to perform abdominal surgery, e.g., gall bladder removal. Laparascopic surgery, like many other types of endoscopic surgery, is often preferred over conventional surgery because laparascopic surgery is less invasive than conventional surgery. As a consequence, laparascopic surgery can be performed in less time and at less cost per procedure than conventional abdominal surgery, and it reduces patient recovery time from weeks to days.

In laparascopic surgery, a plurality of tubes are advanced into the patient's abdomen through percutaneous entry sites. The distal end of each tube is positioned in the patient's abdomen as appropriate for the intended function of the tube. One tube is ordinarily used to establish a working channel through which an appropriate endoscopic instrument, e.g., an endoscopic forceps, scalpel, or retractor, can be advanced to the surgery site to perform the particular procedure. Yet another tube may be used to establish a working channel for insufflating the patient's abdomen, while another tube may be used to establish a working channel for irrigating the surgery site. Also, a tube is typically positioned in the abdomen to establish a working channel for fiber optics, for viewing the interior of the abdomen during the procedure.

To provide for inserting each tube into the patient, a trocar having a sharpened distal end is positioned within the lumen of the tube. The sharpened distal end of the trocar protrudes beyond the distal end of the tube, so that the sharpened distal end can establish a pathway during advancement of the trocar with tube along which the tube can be advanced. When the tube has been positioned as desired, the trocar is retrieved from the lumen of the tube.

Not surprisingly, great care must be taken when advancing the trocar into the patient, to avoid inadvertently cutting or puncturing tissue or organs which should not be cut or punctured. This is particularly true in the case of the first-positioned trocar, which is advanced into the patient prior to positioning a fiber optic into the patient for viewing the interior of the abdomen.

Further, even after a fiber optic has been positioned in the abdomen, the path along which the trocar is to be advanced may not be visible on the video monitor that is connected to the fiber optic, because tissue may be interposed between the fiber optic and the trocar. Thus, the present invention recognizes that when positioning a trocar during endoscopic surgery it would be advantageous to provide a viewing system which can display the path of advancement of the trocar to the surgeon as the trocar is being advanced into the patient.

Accordingly, it is an object of the present invention to provide a trocar which can percutaneously be advanced into a patient by a surgeon who can view the path of advancement on a nearby video monitor. Another object of the present invention is to provide a trocar which is easy to use and safely position within a patient. Yet another object of the present invention is to provide a trocar which is cost-effective to manufacture.

SUMMARY

An endoscopic piercing instrument, preferably a trocar, is provided which can be advanced into a patient while providing a view to the surgeon of the pathway of intended advancement of the trocar, to facilitate safe and proper positioning of the trocar in the patient. One application of the trocar is in laparascopic surgery, wherein a sheath can be positioned in a surrounding relationship with the trocar, and the trocar with sheath can then be advanced into the abdomen of a patient. Once the sheath has been positioned in the abdomen, the trocar is retrieved from the patient, and the sheath establishes a working channel for an endoscopic surgical tool.

In accordance with the present invention, the piercing trocar has a shaft, and the shaft has a distal end and a proximal segment. A cavity is formed in the proximal segment, and a light transmitting member is positioned in the cavity in light communication with the distal end of the shaft. Accordingly, the light transmitting member transmits light which impinges on the distal end of the shaft and which propagates through the shaft to the light transmitting member. Also, a cutting element is attached to the distal end of the shaft for piercing tissue.

Preferably, the light transmitting member is a rigid endoscope, and the endoscope is connected to a video display system. More preferably, the endoscope includes at least one rod lens, and the rod lens is operably connected to a video monitor for displaying an image of the pathway of intended advancement of the trocar as the trocar is advanced into the patient.

In one embodiment, a transparent puncturing head is formed on the distal end of the shaft and is integral to the shaft, and the cutting element is positioned on the puncturing head. As envisioned by the present invention, the puncturing head has a distal portion shaped as a regular triangular pyramid. In other words, the distal portion of the puncturing head has a transverse cross-section which is configured as an equilateral triangle, to permit easily advancing the distal portion of the puncturing head through tissue incident to endoscopic, and more particularly, laparascopic surgery.

Accordingly, the skilled artisan will appreciate that the distal portion of the puncturing head has three generally longitudinal edges. Each edge is sharpened to thereby establish the cutting element.

Alternatively, the cutting element can have three sharpened blades, with the cutting element being embedded in the puncturing head such that a portion of each blade protrudes beyond a respective edge of the distal portion of the puncturing head.

In either embodiment, light from the pathway of intended advancement of the trocar can propagate through the transparent puncturing head and shaft and enter the endoscope. The endoscope then generates an electrical signal representing the image of the pathway of intended advancement and transmits the signal to a video display monitor for display of the pathway of intended advancement on the monitor, which is positioned nearby the surgeon. Accordingly, the surgeon can view the pathway of intended advancement of the trocar on the monitor as the surgeon positions the trocar in the patient, to thereby facilitate safe and proper positioning of the trocar.

In another embodiment, the puncturing head is omitted, and the cutting element includes at least one and preferably four blades that are attached to a distal segment of the shaft. As intended by the present invention, the shaft can be made of steel and at least a central core section of the distal segment is transparent. Also, the shaft has a proximal segment, and a cavity is formed in the proximal segment directly behind the transparent central core section, i.e., the cavity is coaxial with the transparent central core section and abuts the transparent central core section. An endoscope is positioned in the cavity.

The blades extend distally away from the distal segment of the shaft, and are positioned on the shaft such that a line-of-sight is established between the blades from the distal segment of the shaft to a location beyond the blades.

Consequently, as the shaft is advanced into a patient, light which propagates from the pathway of intended advancement of the shaft can pass between the blades and impinge on the distal segment of the shaft. Then, the light can propagate through the transparent central core section of the distal segment of the shaft for reception by the endoscope. The endoscope generates a signal representing the pathway of intended advancement and then transmits the signal to a video display monitor for viewing the pathway of the shaft as it is advanced into the patient.

In another aspect of the present invention, a trocar for endoscopic surgery has a shaft, and the shaft includes a distal end and a proximal segment having a cavity formed therein. The distal end of the shaft includes a cutting element, and a video display system is operationally engaged with the cavity in the proximal segment of the shaft for displaying the image of an object located beyond the cutting element.

In yet another aspect of the present invention, a method for positioning a trocar in a patient's body while viewing the pathway of intended advancement of the trocar is disclosed. The method includes the steps of providing a shaft which has a distal end, and positioning a cutting element on the distal end of the shaft. A video display system that has a light gathering member is engaged with the shaft such that a line-of-sight through the shaft is established from the light gathering member to a location beyond the distal end of the shaft. Thereby, light that propagates from the pathway of intended advancement of the trocar can enter the light gathering member. Then, the distal end of the shaft is advanced into the patient, and an image of the pathway of intended advancement of the trocar is displayed on the video display system.

In yet another embodiment, an endoscopic trocar has an elongated shaft formed with a longitudinal channel therein. The shaft defines an axis and has a distal end, and a puncturing head is formed on the distal end, with the channel extending longitudinally through the puncturing head.

As intended by the alternate embodiment of the present invention, the puncturing head has a distal portion shaped as a partial cone. In other words, the distal portion of the puncturing head has curvilinear surface and a flat surface. Consequently, the puncturing head has a distal apex that is not collinear with the axis of the shaft.

The channel, as stated, is formed through the puncturing head, and terminates at an aperture in the flat surface of the puncturing head. An endoscope is positioned in the channel. If desired, a cutting blade having opposed cutting edges can be positioned on the puncturing head.

The details of the present invention, both as to its construction and operation, can best be understood in reference to the accompanying drawings, in which like numerals refer to like parts, and in which:

BRIEF DESCRIPTION OF THE DRAWINGS

FIG. 10 is another perspective view of the trocar shown in FIG. 9;

FIG. 11 is a cross-sectional view as seen along the line 11—11 in FIG. 9; and

FIG. 12 is an end view of the distal end of the trocar shown in FIG. 9.

DETAILED DESCRIPTION OF THE PREFERRED EMBODIMENT

Figure 1:
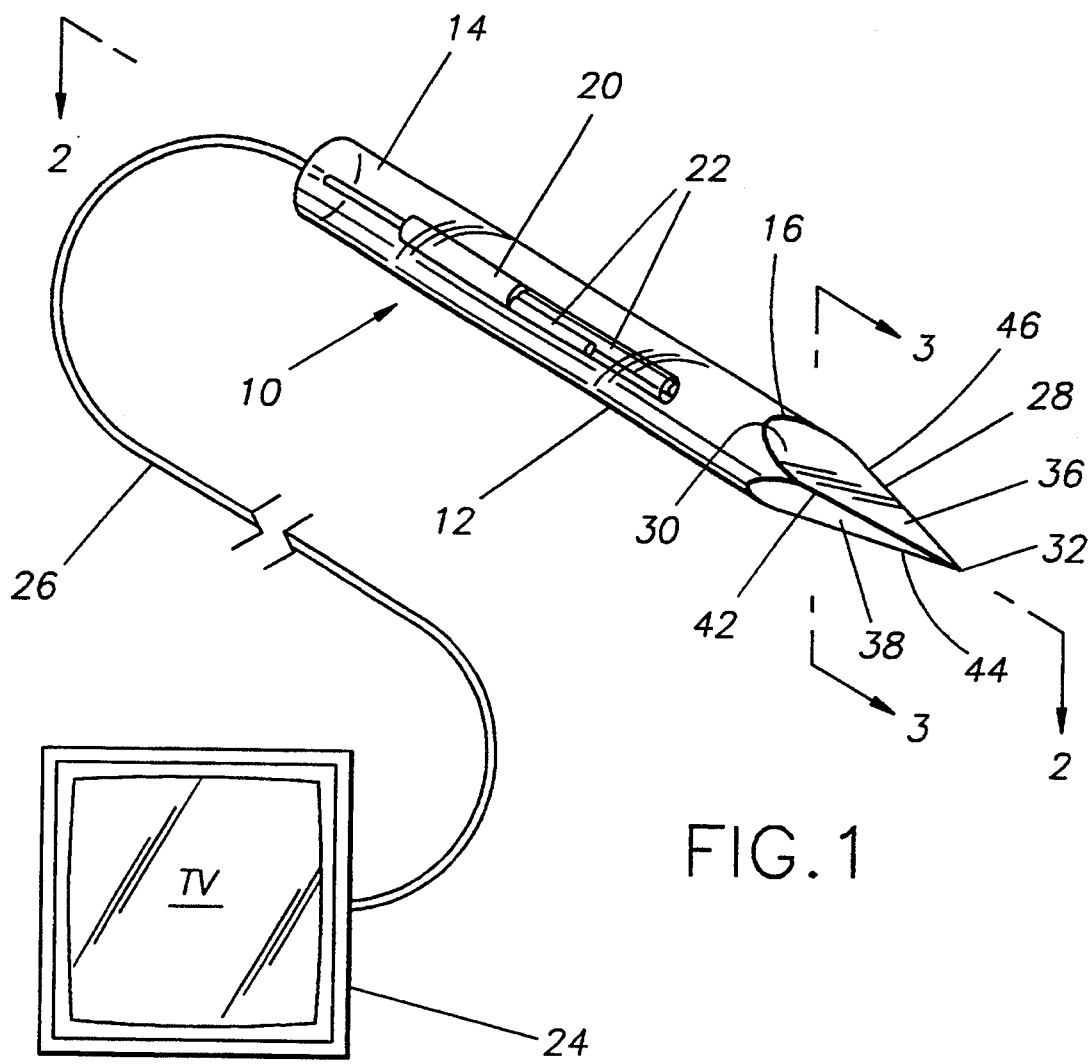
FIG. 1 is a perspective view of the transparent trocar of the present invention.

Referring initially to FIG. 1, a transparent trocar is shown, generally designated 10. As will be more fully disclosed below, the trocar 10 can be advanced into a patient while providing a view to the surgeon of the pathway of intended advancement of the trocar, to facilitate safe and proper positioning of the trocar in the patient during endoscopic and, more particularly, laparascopic surgery. When the trocar 10 is to be used in laparascopic surgery, a sheath (not shown in FIG. 1) such as a Stable Access Cannula ® made by Marlow of Minnesota can be positioned in a surrounding relationship with the trocar 10, and the trocar 10 with sheath advanced into the abdomen of a patient. Once the sheath has been positioned in the abdomen, the trocar 10 is retrieved from the patient, and the sheath establishes a working channel for an endoscopic surgical tool.

As shown in FIG. 1, the trocar 10 has a transparent elongated cylindrical shaft 12. Preferably, the shaft 12 of the trocar 10 is made of a clear, biocompatible, axially rigid material, such as hard plastic, glass, or plexiglass. To improve the capability of the shaft 12 to transmit light, the outer surface of the shaft 12 is polished. When the trocar 10 is to be used for laparascopic surgery, the shaft 12 has a diameter D of about ten millimeters (10 mm), and a length L of about ten centimeters (10 cm). It is to be understood, however, that the trocar 10 can have other diameters, e.g., eight millimeters or twenty millimeters (8 mm or 20 mm).

FIG. 1 further shows that the shaft 12 has a proximal segment 14 and a distal end 16. A cavity 18 is formed in the proximal segment 14 of the shaft 12, and a light gathering member, preferably a rigid endoscope 20, is positioned in the cavity 18. Preferably, the rigid endoscope 20 includes a plurality of rod lens 22. In one presently preferred embodiment, the rigid endoscope 20 can be a rigid surgical endoscope made by Karl Storz Corp.

A video monitor 24 is also shown in FIG. 1, and the video monitor 24 is connected to the endoscope 20 via an electrical line 26. The video monitor 24, endoscope 20, and associated video electronics (not shown) establish a video display system of the type well-known in the art and used to present video images of internal body tissue during endoscopic procedures.

Still referring to FIG. 1, a transparent solid puncturing head 28 is shown formed integrally with the distal end 16 of the shaft 12. The puncturing head 28 is made of the same material as is the shaft 12. Preferably, the puncturing head 28 and shaft 12 are formed integrally together during manufacturing of the trocar 10 by molding processes well-known the art.

Figure 2:
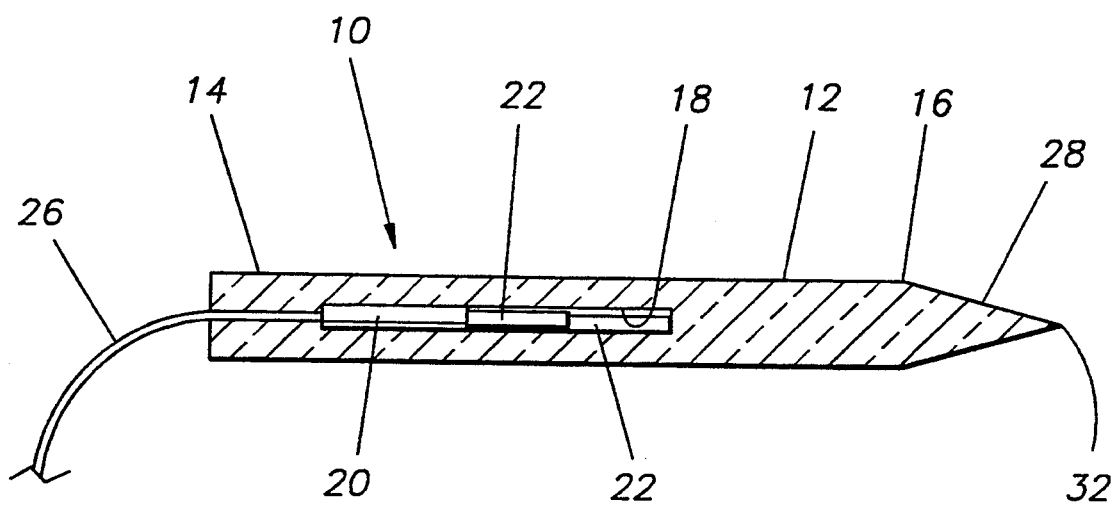
FIG. 2 is a cross-sectional view of the trocar of the present invention, as seen along the line 2—2 in FIG. 1.
Figure 3:
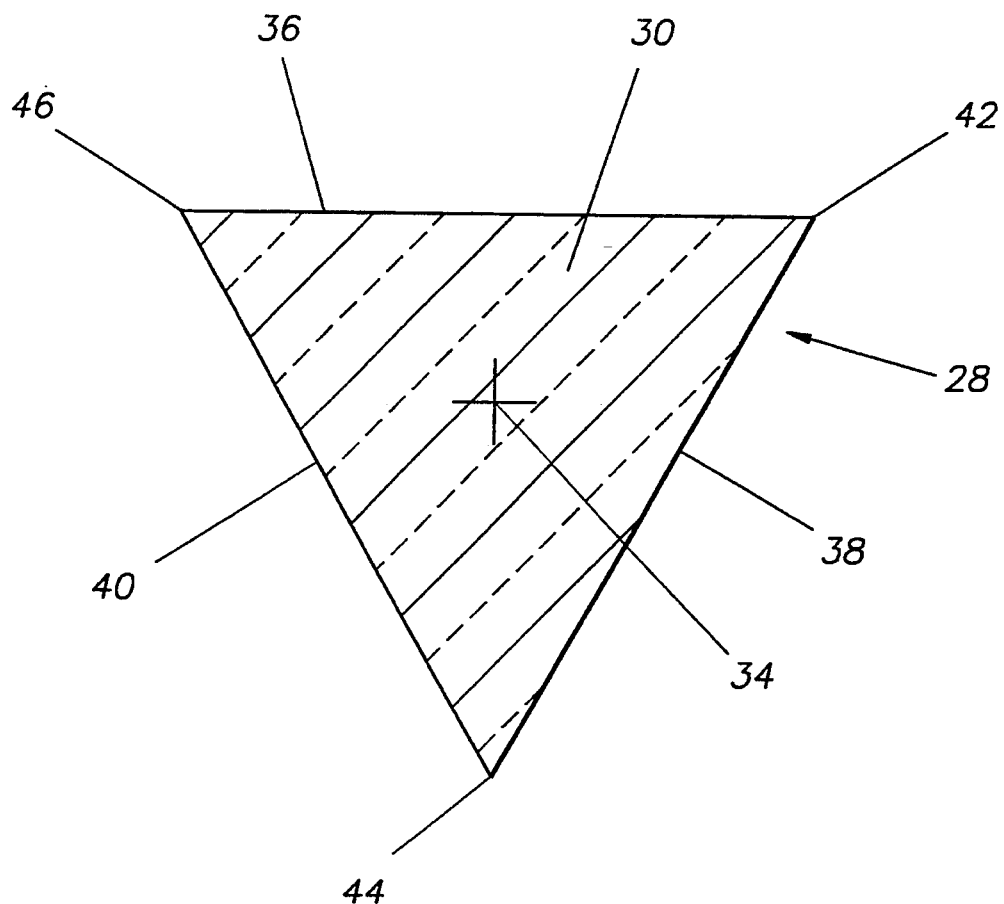
FIG. 3 is a cross-sectional view of the trocar of the present invention, as seen along the line 3—3 in FIG. 1.

In cross-reference to FIGS. 1, 2, and 3, the puncturing head 28 is configured generally as a regular triangular pyramid. Stated differently, the puncturing head 28 has a base 30 (FIG. 3) that is shaped as an equilateral triangle having a geometric center 32, and the puncturing head 28 has an apex 34 (FIG. 2) which, together with the geometric center 32 of the base 30, defines an imaginary line that is perpendicular to the base 30.

Accordingly, in reference to FIGS. 1 and 3, the skilled artisan will appreciate that the puncturing head 28 has three surfaces 36, 38, 40. Three edges 42, 44, 46 are established between the surfaces 36, 38, 40. In accordance with the presently preferred embodiment, the surfaces 36, 38, 40 are polished by means well-known in the art to sharpen the edges 42, 44, 46 and thereby establish a cutting element. Consequently, the trocar 10 can be advanced into tissue, and the edges 42, 44, 46 can cleanly cut the tissue as the trocar 10 is being advanced through the tissue to thereby permit easy advancement of the trocar 10.

Figure 4:
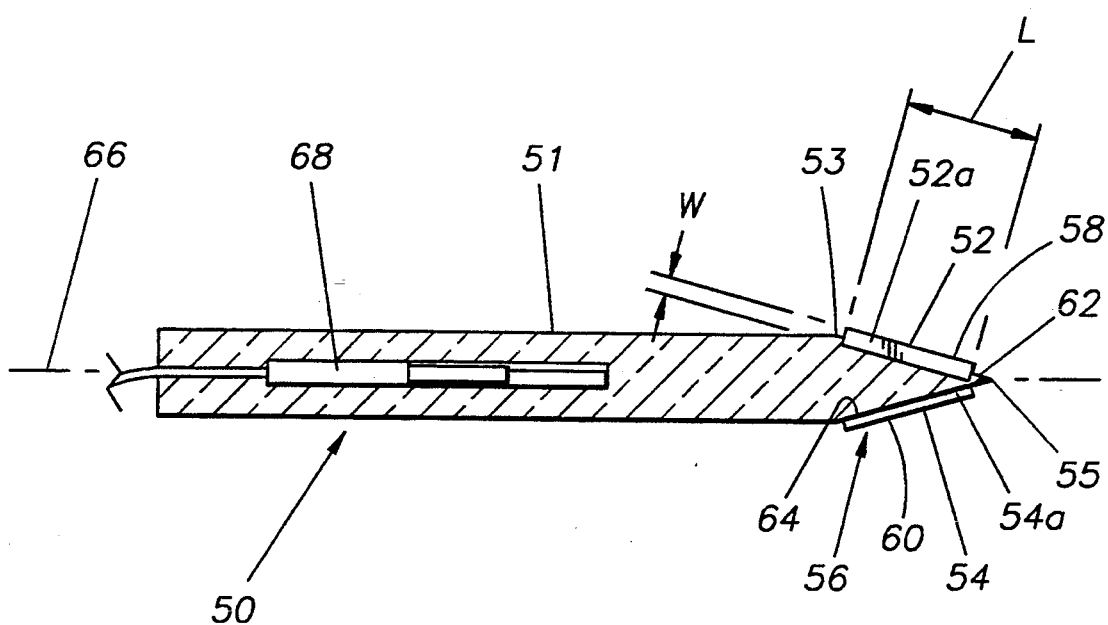
FIG. 4 is a cross-sectional view of an alternative embodiment of the trocar of the present invention, as would be seen along the line 2—2 in FIG. 1, showing cutting blades embedded in the puncturing head.

Now referring to FIG. 4, an alternative embodiment of the trocar of the present invention is shown, generally designated 50. As shown, the trocar 50 has a shaft 51 and is in all essential respects identical to the trocar 10, with the exception that three preferably stainless steel cutting blades (only blades 52, 54 shown in FIG. 4) are embedded in a puncturing head 56. The cutting blades 52, 54 provide greater cutting capability for the puncturing head 56 vis-a-vis the puncturing head 28 shown in FIG. 1. Each cutting blade extends substantially from a distal end 53 of the shaft 51 to near an apex 55 of the puncturing head 56.

Each blade 52, 54 is shaped generally as a thin parallelepiped, similar to a safety razor blade, and the width W of each blade 52, 54 is considerably smaller than the length L of each blade 52, 54. Also, each cutting blade has a respective flat surface 52a, 54a. Each flat blade surface 52a, 54a defines a respective blade plane.

As can be appreciated in reference to FIG. 4, each blade 52, 54 has a respective sharpened cutting edge 58, 60, and each cutting edge 58, 60 protrudes beyond a respective edge (only edges 62, 64 shown in FIG. 4) of the puncturing head 56. The blades 52, 54 are embedded in the puncturing head 56 during manufacturing by molding the blades 52, 56 into the head 56. As the trocar 50 is advanced into tissue, the blades 52, 54 cut the tissue to permit easy advancement of the trocar 50.

Importantly, the cutting blades 52, 54 are preferably oriented such that their respective blade planes are parallel to a longitudinal axis 66 of the trocar 50. Stated differently, the planes defined by the flat surfaces 52a, 54a of the cutting blades 52, 54 intersect each other along the longitudinal axis 66 of the trocar 50, to establish a line-of-sight from the distal end 53 of the shaft 51 to a location beyond the blades 52, 54.

Consequently, the field of view between the blades 52, 54 from the shaft 51 to a location beyond the blades 52, 54 is maximized. In other words, because the flat surfaces 52a, 54a of the cutting blades 52, 54 are positioned parallel to the longitudinal axis 66 of the trocar 50, the amount of light from the pathway of intended advancement of the trocar 50 which can propagate past the blades 52, 54 and impinge on the shaft 51 is maximized. Thus, the amount of light which can enter the distal end 53 of the shaft 51 and propagate through the shaft 51 to an endoscope 68 (for viewing the pathway of intended advancement of the trocar 50 on an associated video monitor) is maximized.

Figure 5:
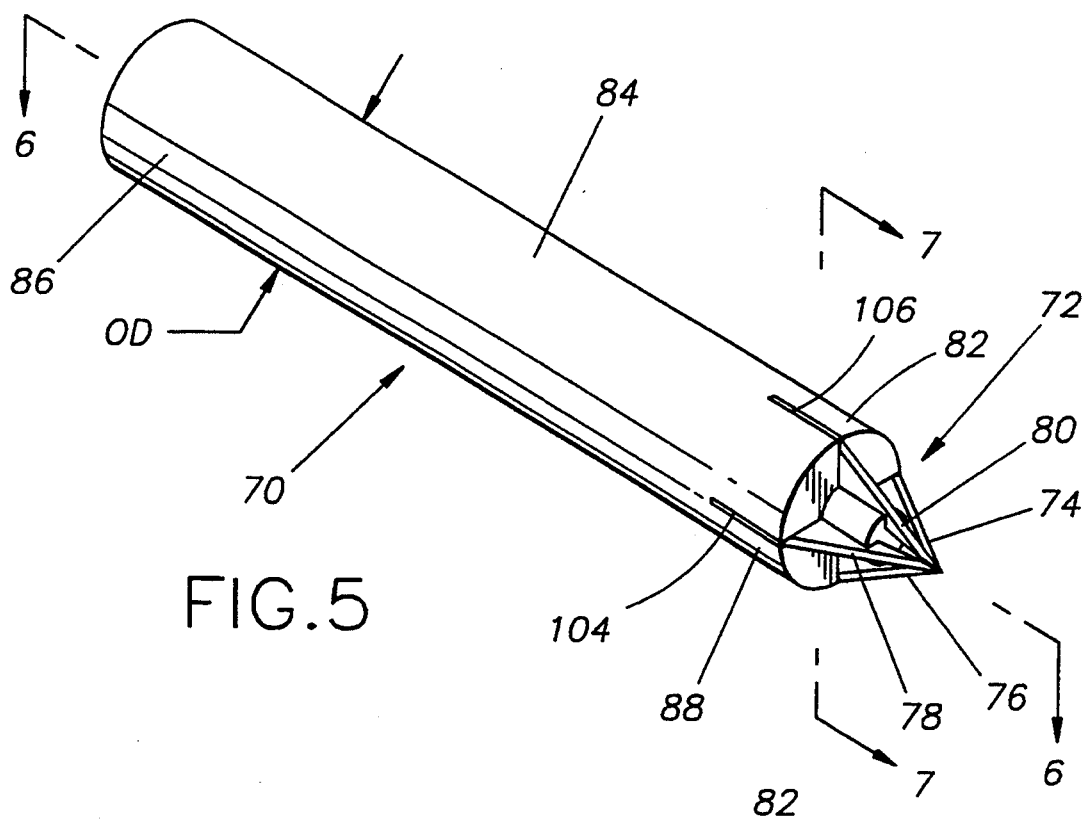
FIG. 5 is a perspective view of an alternate embodiment of the trocar of the present invention, showing cutting blades protruding from the distal end of the shaft.
Figure 6:
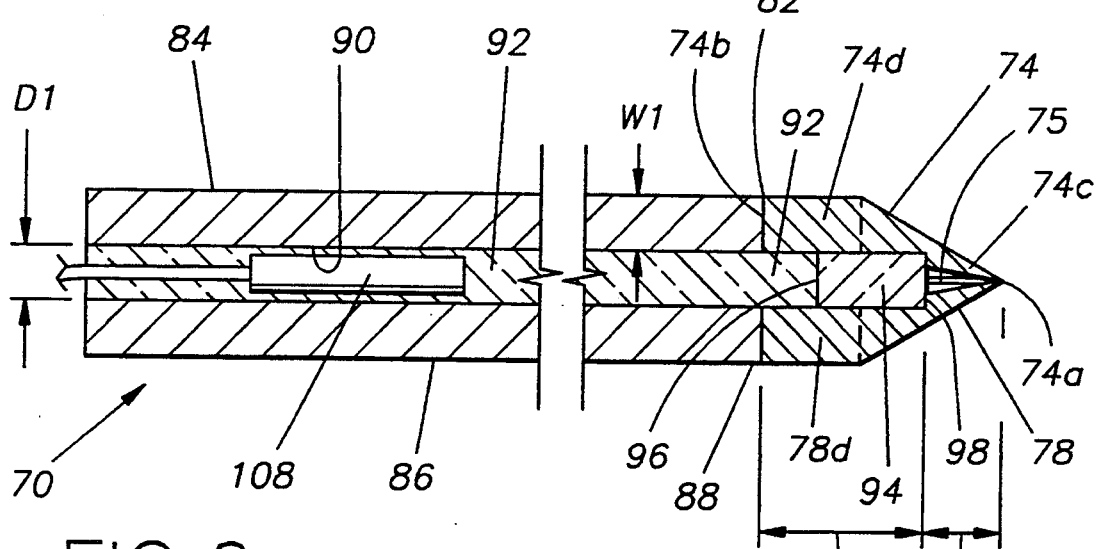
FIG. 6 is a cross-sectional view of the trocar of the present invention, as seen along the line 6—6 in FIG. 5.
Figure 7:
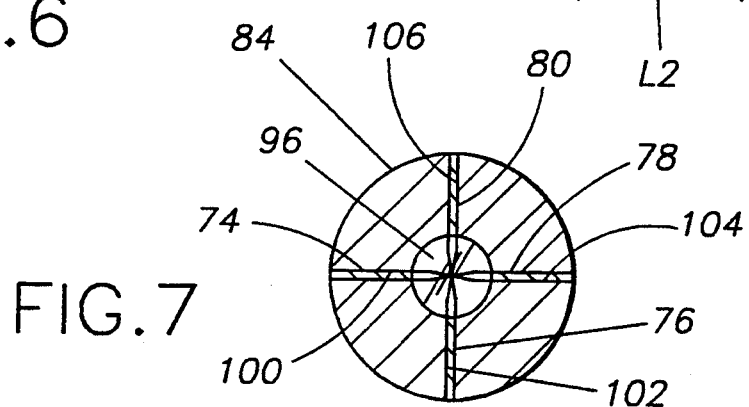
FIG. 7 is a cross-sectional view of the trocar of the present invention, as seen along the line 7—7 in FIG. 5.

FIGS. 5, 6, and 7 show yet another embodiment of the trocar of the present invention, generally designated 70. As shown, the trocar 70 has no cutting head, but has a cutting element 72 comprising a plurality of, preferably four, cutting blades 74, 76, 78, 80 which protrude beyond a distal end 82 of a stainless steel or hard plastic shaft 84. Each blade 74, 76, 78, 80 is identical to the other blades 74, 76, 78, 80. As was the case with the trocars 10, 50 disclosed above, the trocar 70 can have any standard outer diameter OD, e.g., eight, ten, or twenty millimeters (8 mm, 10 mm, 20 mm) or any non-standard size.

As shown in FIGS. 5 and 6, the shaft 84 has a proximal segment 86 and a distal segment 88. FIG. 5 shows that a cavity 90 is formed in the proximal segment 86, and a central core section 92 is formed in the distal segment 88 coaxially with the cavity 90 in an abutting relationship thereto. Both the cavity 90 and central core section 92 have diameters D1 equal to about five millimeters (5 mm).

Also, a transparent plastic or glass plug 94 is positioned in the central core section 92. The plug 94 has a proximal end 96 and a distal end 98, and the ends 96, 98 of the plug 94 are polished, to improve light transmission through the ends 96, 98.

The details of the trocar 70 can best be seen in reference to FIG. 6. Taking the blade 74 as an example, the blade 74 has a pointed distal tip 74a and a flat proximal edge 74b. Further, the blade 74 has a distal segment 74c and a proximal segment 74d. As shown in FIG. 6, the distal segment of each of the blades 74, 76, 78, 80 is tapered inwardly toward the distal tip of the blade, and a space 75 is established between the inside edges of the blades. The pointed distal tips of the blades can be closely spaced from each other and, as shown, are preferably in contact with each other.

As also shown in FIG. 6, taking the blade 74 as an example, the length L1 of the distal segment 74c is equal to about seven millimeters (7 mm), while the length L2 of 35 the proximal segment 74d is equal to about fifteen millimeters (15 mm). Also, the width W1 of the proximal segment 74d is equal to about five millimeters (5 mm).

It is to be understood that the blades 76, 78, 80 are in all essential respects identical to the blade 74. It is to be further understood that while the scale of the dimensions described above may vary, depending upon the size of the trocar 70, the ratios between the lengths L1, L2, W1 will remain about the same as disclosed, to ensure that the blade 74 has adequate strength and axial rigidity to pierce tissue.

FIG. 6 also shows that the blades 74, 76, 78, 80 are fixedly attached to the shaft 84. More specifically, four slots 100, 102, 104, 106 are formed in the shaft 84, with each slot 100, 102, 104, 106 extending longitudinally on the shaft 84, and the proximal segments of the blades 74, 76, 78, 80 (proximal segments 74d, 78d shown in FIG. 6) are positioned in respective slots 100, 102, 104, 106 and then welded or brazed to the shaft 84.

It can be appreciated in cross-reference to FIGS. 5 and 6 that the cutting blades 74, 76, 78, 80 are positioned on the shaft 84 according to the same principle as the cutting blades 52, 54 are positioned relative to the shaft 51 (FIG. 4). More particularly, the cutting blades 74, 76, 78, 80 are positioned on the shaft 84 to maximize the amount of light from the pathway of intended advancement of the trocar 70 which can propagate past the blades 74, 76, 78, 80 and impinge on the distal end 98 of the plug 94.

Light which impinges on the distal end 98 of the plug 94 propagates through the plug 94 and past its proximal end 96. The light then enters the cavity 90. A light gathering member 108 is positioned in the cavity 90 to receive the light and generate an electrical signal representative of the image of the pathway of intended advancement of the trocar 70. This signal is sent to a video display system (not shown in FIGS. 5 and 6) for display of the pathway of intended advancement of the trocar 70 on a video monitor. It is to be understood that in the presently preferred embodiment, the light gathering member 108 is in all essential respects identical to the rigid endoscope 20 shown in FIG. 3.

Figure 9:
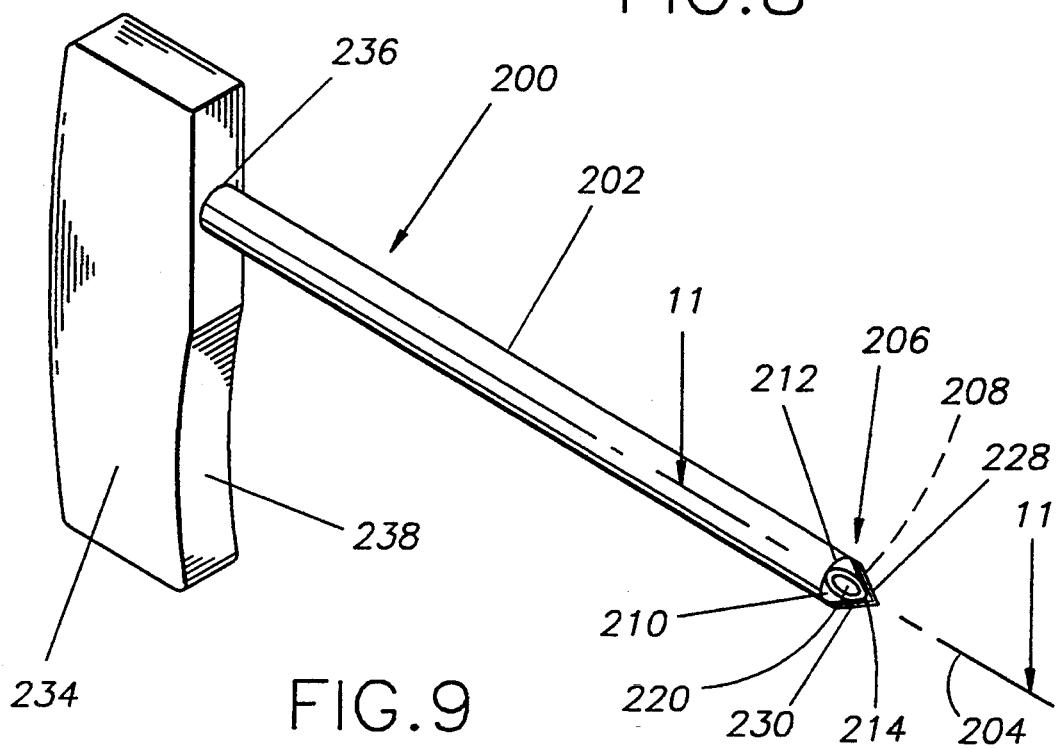
FIG. 9 is a perspective view of an alternate embodiment of the trocar of the present invention.

Now referring to FIGS. 9–12, an alternate embodiment of the trocar of the present invention is shown, generally designated 200. As shown in FIGS. 9, 10, and 11, the trocar 200 has an elongated cylindrical shaft 202 defining an axis 204.

The trocar 200 has a distal end segment configured for cutting tissue. More specifically, as best shown in FIGS. 9 and 10, the trocar 200 has a distal segment 206 that establishes a puncturing head for cutting tissue. As shown, the distal segment 206 is shaped as a partial cone, i.e., the distal segment 206 has a curvilinear surface 208, a flat surface 210, a base 212, and a distal apex 214. As best shown in FIGS. 10 and 12, the apex 214 of the distal segment 206 is distanced from the axis 204 of the shaft 202.

To form the distal segment 206 as shown, the distal segment 206 is cast, molded, forged, or machine as a right circular cone. Then, the distal segment 206 is machined or ground to establish the flat surface 210. As can be appreciated in reference to FIGS. 9–12, the shaft 202 and distal segment 206 are preferably made of a unitary piece of material, e.g., stainless steel, aluminum, or hard plastic or composite material.

FIG. 11 best shows that a hollow channel 216 is longitudinally formed in the shaft 202 and distal segment 206. The channel 216 terminates at an aperture 218 that is formed in the flat surface 210 of the distal segment 206. An endoscope 220, which is in all essential respects identical to the endoscope 20 shown in FIG. 3, is disposed in the channel 216, with a distal end 222 of the endoscope 220 positioned adjacent the aperture 218.

FIG. 11 also shows that a cutting blade 224 is glued to the distal segment 206 within a slot 226 which is formed in the distal segment 206. Preferably, the blade 224 is a metal or hard plastic blade that has opposed sharpened cutting edges 228, 230 (best shown in FIG. 10). As shown in FIG. 10, each cutting edge 228, 230 of the blade 224 protrudes outwardly from the curved surface 208 of the distal segment 206 to cut tissue and thereby aid advancing the trocar 200 through tissue. If desired, the edge 232 of the flat surface 210 can be sharpened, to further aid in advancing the trocar 200 through tissue.

Referring back to FIG. 9, a metal or plastic handle 234 is attached to a proximal end segment 236 of the shaft 202. Preferably, the proximal end segment 236 is embedded in the handle 234. The endoscope 220 extends through the channel 216 and into the handle 234, and a video display system (not shown) can be operably engaged with the endoscope 220.

Furthermore, the handle 234 has a curved finger surface 238. Accordingly, a person can firmly grasp the handle 234 with his fingers against the gripping surface 238 and advance the trocar 200 through tissue.

Figure 8:
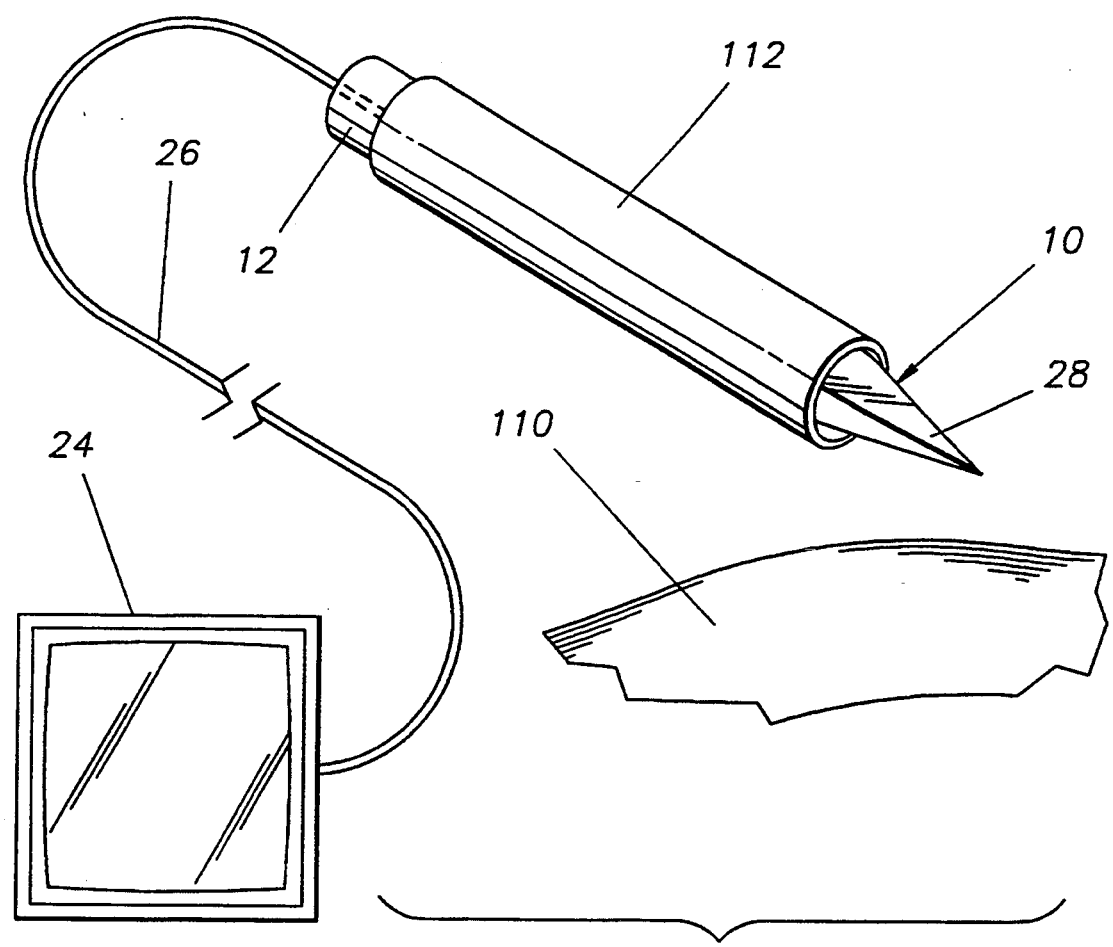
FIG. 8 is a perspective view of the trocar of the present invention, shown in one intended environment.

In the operation of the trocar 10, reference is made to FIG. 8. Initially, a small pilot hole is made in the abdomen of a patient 110 by means well-known in the laparascopic surgery art. More specifically, an insufflation needle is advanced into the abdomen of the patient 110 to inflate the abdomen with air. Then, the insufflation needle is retrieved from the patient 110, and the trocar 10 advanced into the patient 110 through the opening created by the insufflation needle.

As shown, a hollow sleeve 112, e.g., a Stable Access Cannula ® made by Marlow of Minnesota, is positioned around the trocar 10, and the trocar 10 can reciprocate within the sleeve 112. Alternatively, the trocar 10 can be spring-loaded in a sleeve such that the trocar 10 is urged distally outwardly from the sleeve when the trocar 10 abuts tissue during advancement of the trocar, to permit the trocar 10 to cut the tissue. When the trocar 10 encounters little or no resistance, the trocar 10 slides back proximally within the sleeve, to avoid inadvertently puncturing tissue which is not to be punctured. The spring-loaded structure described above (with a prior art opaque trocar) is well known in the prior art.

As the trocar 10 with sleeve 112 is advanced into the patient 110, the puncturing head 28 of the trocar 10 cuts through tissue. During advancement of the trocar 10, light from the pathway of intended advancement of the trocar 10 can propagate through the transparent puncturing head 28 and transparent shaft 12 and impinge upon the endoscope 20 (FIG. 1). The endoscope 20 in turn generates an electrical signal representative of the pathway of intended advancement of the trocar 10, and sends this signal to the video monitor 24 via the line 26 for display of the pathway of intended advancement on the video monitor 24. The surgeon can view the pathway of intended advancement of the trocar 10 on the monitor 24 to safely and properly position the trocar 10 with sleeve 112 inside the patient 24. Upon positioning the trocar 10 with sleeve 112 as desired, the trocar 10 is retrieved from the patient 110, and the sleeve 112 remains in place inside the patient 110 to establish a working channel for an endoscopic instrument. It is to be understood that the operation of each of the trocars 50, 70, 200 is in all essential respects identical to the operation of the trocar 10.

While the particular trocar as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. An endoscopic piercing instrument, comprising:
   a transparent shaft having a distal end configured for cutting tissue and a proximal segment, the proximal segment having a cavity formed therein;
   a light transmitting member positioned in the cavity in light communication with the distal end of the shaft for transmitting light which impinges on the distal end and propagates to the light transmitting member through said transparent shaft; and
   a pyramidal puncturing head formed from a plurality of contiguous flat triangular surfaces on the shaft at the distal end, the puncturing head comprising a plurality of sharpened blades each aligned with and secured to an edge between said contiguous flat triangular surfaces.

2. The instrument of claim 1, wherein the light transmitting member is a rigid endoscope, and the endoscope is connected to a video display system.

3. The instrument of claim 2, wherein the endoscope includes at least one rod lens.

4. The instrument of claim 1, wherein a portion of the puncturing head is generally configured as a regular triangular pyramid.

5. A trocar for endoscopic surgery, comprising:
   a shaft having a distal end and a proximal segment having a cavity formed therein;
   a cutting element attached to the distal end of the shaft;
   a video display system operationally connected to light receiving means in the interior of the cavity formed in the proximal segment of the shaft for displaying the image of an object located beyond the cutting element;
   a transparent puncturing head formed on the distal end of the shaft, the puncturing head having a polished distal portion configured generally as a pyramid having a plurality of contiguous triangular surfaces; and
   plurality of sharpened blades each aligned with and secured to an edge between said contiguous triangular surfaces.

6. The trocar of claim 5, wherein light receiving mean includes a rigid endoscope positioned in the cavity and the video display system a video monitor operably connected to the rigid endoscope.

7. The trocar of claim 5 wherein said distal portion is generally configured as a regular triangular pyramid.

* * * * *